(12) United States Patent
Ohkubo

(10) Patent No.: US 8,119,996 B2
(45) Date of Patent: Feb. 21, 2012

(54) QUANTUM EFFICIENCY MEASUREMENT APPARATUS AND QUANTUM EFFICIENCY MEASUREMENT METHOD

(75) Inventor: Kazuaki Ohkubo, Kusatsu (JP)

(73) Assignee: Otsuka Electronics Co., Ltd., Osaka (JP)

( * ) Notice: Subject to any disclaimer, the term of this patent is extended or adjusted under 35 U.S.C. 154(b) by 244 days.

(21) Appl. No.: 12/520,975

(22) PCT Filed: Jan. 20, 2009

(86) PCT No.: PCT/JP2009/050734
§ 371 (c)(1),
(2), (4) Date: Jun. 23, 2009

(87) PCT Pub. No.: WO2010/084566
PCT Pub. Date: Jul. 29, 2010

(65) Prior Publication Data
US 2011/0155926 A1    Jun. 30, 2011

(51) Int. Cl.
*G01J 1/04* (2006.01)
(52) U.S. Cl. .............. 250/459.1; 250/336.1; 250/372
(58) Field of Classification Search ............. 250/336.1, 250/372, 459.1
See application file for complete search history.

(56) References Cited

U.S. PATENT DOCUMENTS

| | | | | |
|---|---|---|---|---|
| 5,430,540 A * | 7/1995 | Ohkubo | .............. | 356/236 |
| 6,020,959 A | 2/2000 | Imura | | |
| 6,654,119 B1 | 11/2003 | Gould et al. | | |
| 6,995,355 B2 * | 2/2006 | Rains et al. | ............. | 250/228 |
| 2003/0227627 A1 | 12/2003 | Imura et al. | | |
| 2007/0242264 A1 | 10/2007 | Ohkubo | | |

FOREIGN PATENT DOCUMENTS

| | | |
|---|---|---|
| EP | 1643225 | 4/2006 |
| JP | 9-292281 | 11/1997 |
| JP | 10-142152 | 5/1998 |
| JP | 10-160570 | 6/1998 |
| JP | 10-293063 | 11/1998 |
| JP | 2000-19114 | 1/2000 |
| JP | 2003-215041 | 7/2003 |
| JP | 2008-292497 | 12/2008 |
| JP | 2009-103654 | 5/2009 |
| TW | 432203 B | 5/2001 |
| WO | WO 2007/122674 | 11/2007 |

OTHER PUBLICATIONS

Kazuaki Ohkubo et al., "Absolute Fluorescent Quantum Efficiency of NBS Phosphor Standard Samples", Journal of the Illuminating Engineering Institute of Japan, The Illuminating Engineering Institute of Japan, Feb. 1999, vol. 83, No. 2, pp. 87-93 (w/ English abstract).

(Continued)

*Primary Examiner* — David P Porta
*Assistant Examiner* — Djura Malevic
(74) *Attorney, Agent, or Firm* — Ditthavong Mori & Steiner, P.C.

(57) ABSTRACT

A sample that is an object whose quantum efficiency is to be measured, and a standard object having a known reflectance characteristic are each attached to a sample window provided in a plane mirror. Based on respective spectrums measured by a spectrometer in respective cases where the sample is attached and the standard object is attached, the quantum efficiency of the sample is measured. The plane of an opening of an observation window is made substantially coincident with the exposed surface of the sample or standard object, so that direct incidence, on the observation window, of the fluorescence generated from the sample receiving an excitation light and the excitation light reflected from sample is prevented.

10 Claims, 10 Drawing Sheets

OTHER PUBLICATIONS

Kosei Oshima. Otsuka Electronics Co., Ltd., "Optical Property Evaluation for OLED", Material Stage vol. 8, No. 1, 2008, pp. 41-44.
Japanese Office Action for corresponding JP Application No. 2009-527379, Oct. 19, 2010.
Taiwanese Office Action for corresponding TW Application No. 098120568, Jun. 7, 2011.
Extended European Search Report for corresponding EP Application No. 09709437.9-1234/2315003, Sep. 5, 2011.

* cited by examiner

QUANTUM EFFICIENCY MEASUREMENT APPARATUS AND QUANTUM EFFICIENCY MEASUREMENT METHOD

TECHNICAL FIELD

The present invention relates to an apparatus and a method for measuring the quantum efficiency of an object to be measured.

BACKGROUND ART

In recent years, development of fluorescent lamp and display has advanced swiftly. With such development, the quantum efficiency has become of interest as an index for more accurately evaluating the performance of a phosphor used for the lamp and display. In general, the quantum efficiency refers to the ratio of the number of photons of fluorescence to the number of photons absorbed by an object to be measured (typically phosphor).

As a typical method for measuring such a quantum efficiency, "Absolute Fluorescent Quantum. Efficiency of NBS Phosphor Standard Samples" by Ohkubo and Shigeta discloses a measurement optical system for the phosphor quantum efficiency. Alternatively to the configuration as disclosed, Japanese Patent Laying-Open Nos. 09-292281 (Patent Document 1), 10-142152 (Patent Document 2) and 10-293063 (Patent Document 3) for example propose configurations and methods for measuring the quantum efficiency.

The quantum efficiency measurement apparatuses according to the above-referenced conventional technologies all use an integrating sphere for trapping fluorescence emitted from an object to be measured (phosphor). Generally, the fluorescence emitted from a phosphor is weak. It is therefore preferable to use an integrating sphere having a smaller diameter in order to enhance the measurement accuracy.

In such an integrating sphere, a baffle is provided for hindering fluorescence emitted from a phosphor and/or an excitation light reflected from the surface of the phosphor from directly entering a detector.

Patent Document 1: Japanese Patent Laying-Open No. 09-292281
Patent Document 2: Japanese Patent Laying-Open No. 10-142152
Patent Document 3: Japanese Patent Laying-Open No. 10-293063
Non-Patent Document 1: Ohkubo and Shigeta, "Absolute Fluorescent Quantum Efficiency of NBS Phosphor Standard Samples," Journal of the Illuminating Engineering Institute of Japan, The Illuminating Engineering Institute of Japan, 1999, Vol. 83, No. 2, pp. 87-93

DISCLOSURE OF THE INVENTION

Problems to be Solved by the Invention

In the case where an integrating sphere with a smaller diameter is used, however, the influence of light absorption by the baffle is relatively larger, resulting in a possibility that the measurement accuracy is negatively impacted.

The present invention has been made to solve the problem above, and an object of the invention is to provide a quantum efficiency measurement apparatus and a quantum efficiency measurement method with which the quantum efficiency can be measured with a higher accuracy.

Means for Solving the Problems

A quantum efficiency measurement apparatus according to an aspect of the present invention includes a hemispheric portion with an inner surface having a light diffuse reflection layer, and a plane mirror disposed to pass through a substantial center of curvature of the hemispheric portion and close an opening of the hemispheric portion. The plane mirror includes a first window provided at a position of the substantial center of curvature of the hemispheric portion for attaching an object to be measured to the first window, and a second window provided at a position apart by a predetermined distance from the first window. The quantum efficiency measurement apparatus further includes: a spectrometer for measuring a spectrum in the hemispheric portion through the second window; a light source for applying an excitation light, through a third window provided in the hemispheric portion, at a predetermined angle with respect to a normal to the plane mirror toward the first window; and a processor for calculating a quantum efficiency of the object to be measured, based on a first spectrum measured by the spectrometer in a case where the object to be measured is disposed at the first window, and a second spectrum measured by the spectrometer in a case where a standard object having a known reflectance characteristic is disposed at the first window instead of the object to be measured.

Preferably, the first window is configured such that the object to be measured can be attached in a state where an exposed surface of the object to be measured substantially coincides with a surface of the plane mirror, the surface of the plane mirror being located on an inner side of the hemispheric portion.

Preferably, the second window includes a light transmission diffusion member disposed between an inside of the hemispheric portion and the spectrometer.

A quantum efficiency measurement apparatus according to another aspect of the present invention includes a hemispheric portion with an inner surface having a light diffuse reflection layer, and a plane mirror disposed to pass through a substantial center of curvature of the hemispheric portion and close an opening of the hemispheric portion. The plane mirror includes a first window provided near the substantial center of curvature of the hemispheric portion and a second window provided at a position apart by a predetermined distance from the first window. The quantum efficiency measurement apparatus further includes a light source for applying an excitation light through the first window toward an object to be measured disposed in a state where at least a part of the object to be measured is exposed in the hemispheric portion, and a spectrometer for measuring a spectrum in the hemispheric portion through the second window. The second window restrains light from the object to be measured from directly entering the spectrometer. The quantum efficiency measurement apparatus further includes a processor for calculating a quantum efficiency of the object to be measured, based on a first spectrum measured by the spectrometer in a case where the object to be measured is disposed in the hemispheric portion, and a second spectrum measured by the spectrometer in a case where a standard object having one of a known reflectance characteristic and a known transmittance characteristic is disposed in the hemispheric portion instead of the object to be measured.

Preferably, the second window is an opening having a larger diameter on an outer side of the hemispheric portion than a diameter of the opening on an inner side of the hemispheric portion.

Preferably, the hemispheric portion includes a third window provided at a position where the hemispheric portion intersects with a normal that is normal to the plane mirror and passes through the substantial center of curvature of the hemispheric portion, for attaching the object to be measured and the standard object to the third window, and the light source is disposed to apply the excitation light at a predetermined angle with respect to the normal to the plane mirror toward the third window.

Preferably, the object to be measured is a liquid enclosed in a transparent container and is disposed on an optical axis of the light source.

More preferably, the object to be measured is entirely contained in the hemispheric portion.

Preferably, the hemispheric portion includes a third window provided at a position where the hemispheric portion intersects with a normal that is normal to the plane mirror and passes through the substantial center of curvature of the hemispheric portion, for attaching the object to be measured and the standard object to the third window. The first window is provided at a position of the substantial center of curvature of the hemispheric portion on the plane mirror, and the object to be measured is a liquid enclosed in a tubular container, a surface of the tubular container that is attached to the third window is formed of a transparent material, and a remaining part of the tubular container is formed of a light-reflective member.

A quantum efficiency measurement method according to still another aspect of the present invention includes the steps of: preparing an apparatus including a hemispheric portion with an inner surface having a light diffuse reflection layer, and a plane mirror disposed to pass through a substantial center of curvature of the hemispheric portion and close an opening of the hemispheric portion; attaching an object to be measured to a first window provided at a position of the plane mirror, the position including the substantial center of curvature of the hemispheric portion; applying an excitation light, through a third window provided in the hemispheric portion, at a predetermined angle with respect to a normal to the plane mirror toward the object to be measured; measuring, as a first spectrum, a spectrum in the hemispheric portion in a case where the object to be measured is attached, through a second window provided at a position of the plane mirror, the position being apart by a predetermined distance from the first window; attaching a standard object having a known reflectance characteristic to the first window; applying the excitation light through the third window, at the predetermined angle with respect to the normal to the plane mirror toward the standard object; measuring, as a second spectrum, a spectrum in the hemispheric portion through the second window in a case where the standard object is attached; and calculating a quantum efficiency of the object to be measured, based on the first spectrum and the second spectrum.

Effects of the Invention

In accordance with the present invention, the quantum efficiency can be measured with a higher accuracy.

Figure 1:
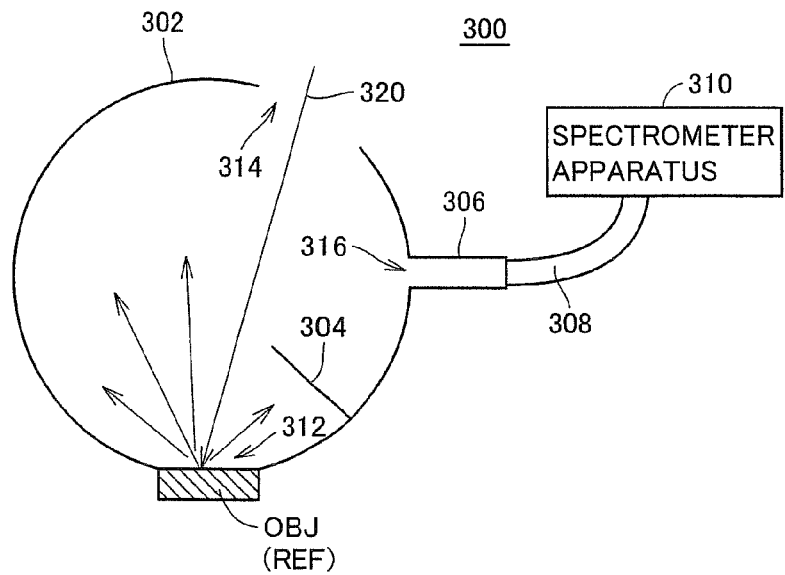
FIG. 1 is a schematic configuration diagram of a quantum efficiency measurement apparatus relevant to a first embodiment of the present invention.

DESCRIPTION OF THE REFERENCE SIGNS 1, 1A hemispheric portion, 1a light diffuse reflection layer, 2, 9 sample window, 3, 13 observation window, 4, 10, 12 light source window, 5, 5A, 5B, 5C plane mirror, 5a reflection surface, 6 spectrometer, 6a attachment portion, 6b fiber end, 6c reflection portion, 6d optical fiber, 6e detector, 7 light source, 7a lamp, 7b collective optical system, 14 light transmission diffusion member, 15, 15A seal member, 16, 16A, 16B transparent cell, 100 integrating hemisphere, 102 base portion, 104 rotational shaft, 200, 200A processor, 202 switch unit, 204, 206 buffer, 208, 210 selection unit, 212, 222 multiplication unit, 214, 224 integration unit, 216, 226 division unit, 218 initial setting holding unit, 220 addition and subtraction unit, 300, 350 quantum efficiency measurement apparatus, 302, 352 integrating sphere, 304, 358 baffle, 306, 360 light receiving unit, 308, 362 optical fiber, 310, 364 spectrometer apparatus, 312 sample window, 314, 366 light source window, 316, 368 observation window, 320, 370 excitation light, 354 support, 356 transparent container, Ax1, Ax2, Ax3 optical axis, L1 excitation light, OBJ, OBJ1, OBJ2 sample, REF, REF1, REF2 standard object, SYS1, SYS1A, SYS2, SYS3, SYS3A, SYS3B quantum efficiency measurement apparatus

BEST MODES FOR CARRYING OUT THE INVENTION

Embodiments of the present invention will be described in detail with reference to the drawings. Like or corresponding components in the drawings are denoted by like reference characters, and a description thereof will not be repeated.

First Embodiment

<Related Art>

For the sake of facilitating understanding of a quantum efficiency measurement apparatus according to the present embodiment, a quantum efficiency measurement apparatus relevant to the present embodiment will be described first with reference to FIG. 1.

Quantum efficiency measurement apparatus 300 relevant to the present embodiment shown in FIG. 1 measures the quantum efficiency of an object to be measured such as phosphor (also referred to as "sample OBJ" hereinafter). Specifically, quantum efficiency measurement apparatus 300 includes an integrating sphere 302, a baffle 304, a light receiving unit 306, an optical fiber 308, and a spectrometry apparatus 310. In quantum efficiency measurement apparatus 300, sample OBJ is attached to a sample window 312 provided in integrating sphere 302, and an excitation light 320, which is emitted through a light source window 314 from a light source (not shown) provided outside integrating sphere 302, is applied to sample OBJ. As excitation light 320, monochromatic ultraviolet radiation in 200 to 400 nm is used in the case of a low-pressure mercury fluorescent lamp, and monochromatic ultraviolet or visible radiation in 300 to 600 nm or the like is used in the field of LED (Light Emitting Diode). Sample OBJ receives excitation light 320 to emit fluorescence. The fluorescence radiated from sample OBJ is multiple-reflected from the inner surface of integrating sphere 302 and accordingly integrated (made uniform). A part of the applied excitation light 320 is reflected from sample OBJ, and this reflected excitation light 320 is also multiple-reflected in integrating sphere 302.

Light receiving unit 306 extracts, through an observation window 316 provided in integrating sphere 302, a part of the light in integrating sphere 302 to direct the extracted light to spectrometry apparatus 310 via optical fiber 308. The portion facing observation window 316 of light receiving unit 306 is generally provided with a light transmission diffusion member. In general, the view angle characteristic at observation window 316 is thus made closer to ideal diffusion characteristic, and the illuminance (light spectrum) of the light from the whole inner wall surface of integrating sphere 302 is directed to optical fiber 308.

Spectrometry apparatus 310 measures the spectrum of the light extracted by light receiving unit 306. Namely, spectrometry apparatus 310 measures the illuminance (light spectrum) on the inner wall surface of integrating sphere 302.

Measurement similar to the above-described one is also performed on a standard object REF having a known reflectance characteristic that is attached instead of sample OBJ. Based on the spectrum measured for sample OBJ as attached and the spectrum measured for standard object REF as attached, the quantum efficiency of sample OBJ is calculated.

As described above, integrating sphere 302 can be used to accurately measure the quantum efficiency even if sample OBJ does not have the ideal diffuse reflection characteristic such as sample OBJ whose surface has specularity. Further, since integrating sphere 302 itself functions as a light shielding container, an effect of restraining the influence of the external light is also obtained.

Regarding quantum efficiency measurement apparatus 300, however, a measurement error occurs if the fluorescence generated from sample OBJ and a part of excitation light 320 reflected from sample OBJ directly enter observation window 316. Therefore, baffle 304 is provided between sample window 312 and observation window 316.

The fluorescence from a phosphor is generally weak. Therefore, in order to enhance the measurement accuracy, it is preferable to use integrating sphere 302 having a smaller diameter. In the case where integrating sphere 302 with a smaller diameter is used, however, the influence of light absorption by baffle 304 is relatively larger, resulting in a possibility that the measurement accuracy is negatively impacted. In other words, a problem is that baffle 304 could be a factor of the measurement error, since baffle 304 hinders interreflection on the inner wall surface of integrating sphere 302, and light absorption by baffle 304 decreases the integration efficiency.

<Apparatus Configuration>

Figure 2:
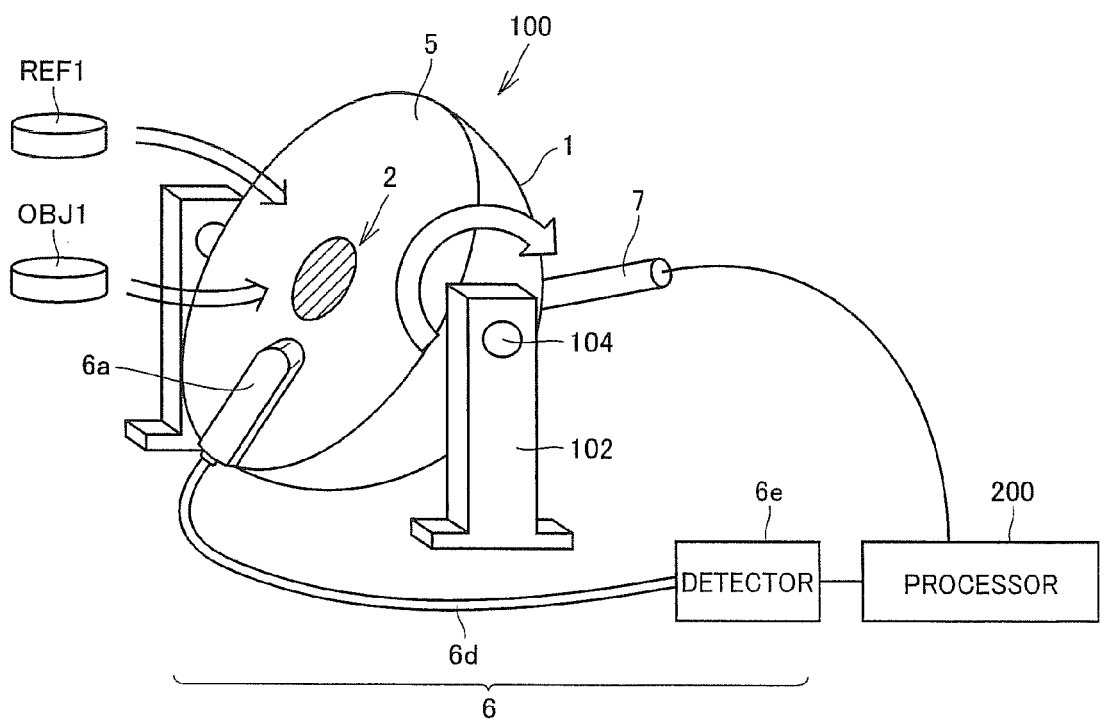
FIG. 2 is an external view of a quantum efficiency measurement apparatus according to the first embodiment of the present invention.
Figure 3:
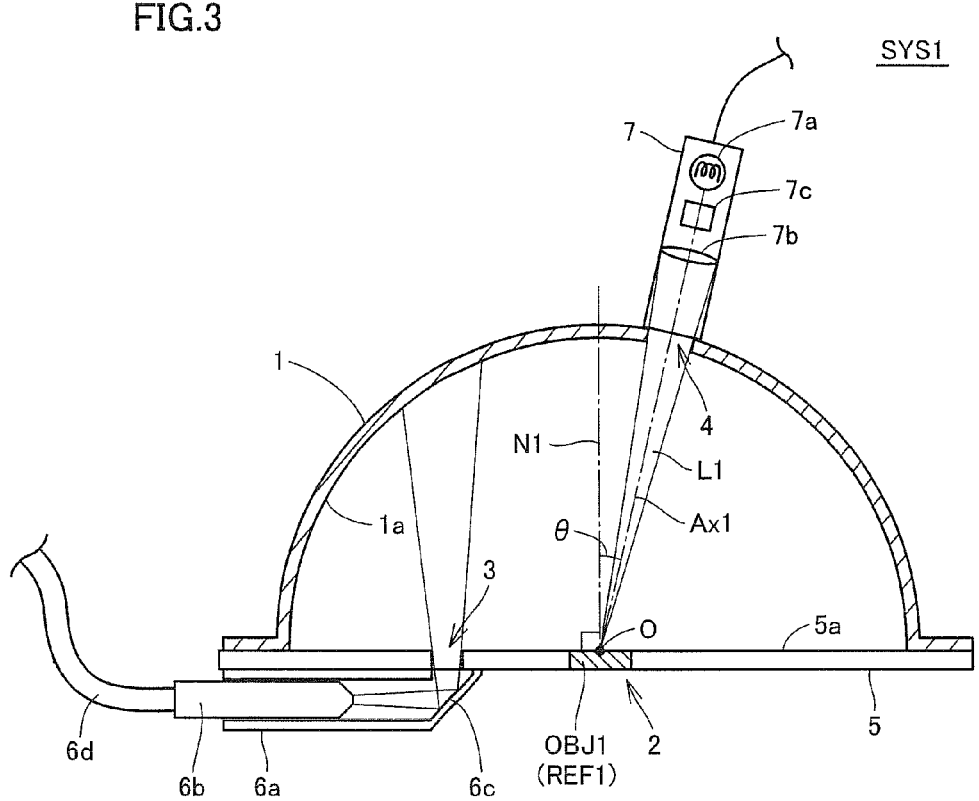
FIG. 3 is a cross section showing main components of the quantum efficiency measurement apparatus according to the first embodiment of the present invention.

Referring next to FIGS. 2 and 3, a quantum efficiency measurement apparatus SYS1 according to the present embodiment will be described.

Quantum efficiency measurement apparatus SYS1 shown in FIG. 2 includes an integrating hemisphere 100 and a processor 200. As shown in FIG. 3, integrating hemisphere 100 is formed of a hemispheric portion 1 and a disk-shaped plane mirror 5 disposed to close the opening of hemispheric portion 1. Hemispheric portion 1 is rotatably coupled to a base portion 102 via a rotational shaft 104. Quantum efficiency measurement apparatus SYS1 further includes a spectrometer 6 for measuring the illuminance (light spectrum) on the inner wall surface of hemispheric portion 1, and a light source 7 generating an excitation light L1.

In quantum efficiency measurement apparatus SYS1 according to the present embodiment, a sample OBJ1 that is an object whose quantum efficiency is to be measured and a standard object REF1 having a known reflectance characteristic are each attached to a sample window 2 provided in plane mirror 5, as described hereinlater. The quantum efficiency of sample OBJ1 is then measured based on respective spectrums measured by spectrometer 6 in respective cases where sample OBJ1 is attached and standard object REF1 is attached.

Quantum efficiency measurement apparatus SYS1 according to the present embodiment is typically suitable for measurement of the quantum efficiency of a solid sample such as a phosphor for a florescent lamp and a phosphor for an LED. Standard object REF1 is typically an object having its surface to which barium sulfate is applied. Each of sample OBJ1 and standard object REF1 is shaped to nearly conform to the diameter of sample window 2. This is for the reason that it is preferable to allow integrating hemisphere 100 to function as a light shielding container for the purpose of avoiding influence of the external light on the measurement accuracy. As long as the diameter of sample OBJ1 and standard object REF1 each is nearly identical to the diameter of sample window 2, respective shapes of other portions of the sample and the standard object are not particularly limited to specific ones.

As shown in FIG. 3, the inner surface (inner wall) of hemispheric portion 1 is provided with a light diffuse reflection layer 1a. Light diffuse reflection layer 1a is typically formed by applying or spraying a light diffusion material such as barium sulfate or PTFE (polytetrafluoroethylene).

Hemispheric portion 1 is provided with a light source window 4 for guiding excitation light L1 radiated from light source 7 provided outside hemispheric portion 1 to the inside of hemispheric portion 1. Excitation light L1 is applied toward sample OBJ1 or standard object REF1 along an optical axis Ax1 with an angle θ with respect to a normal N1 to plane mirror 5. This is for the purpose of preventing a specular reflection component from being generated on sample OBJ1 or standard object REF1 from excitation light L1 from light source 7. Namely, this is for the purpose of guiding a part of excitation light L1 applied from light source 7 and then reflected from sample OBJ1 or standard object REF1, in a direction different from the direction of optical axis Ax1 that is the incident light path. Preferably, angle θ is approximately 5°.

Plane mirror 5 is disposed to pass through a substantial center of curvature O of hemispheric portion 1 and close the opening of hemispheric portion 1. Here, center of curvature O of hemispheric portion 1 typically refers to the geometric center of the inner surface side of hemispheric portion 1. A reflection surface (mirror surface) 5a is formed at least on the side, located on the inner surface side of hemispheric portion 1, of plane mirror 5.

Plane mirror 5 is provided with sample window 2 and observation window 3 that are each able to communicate with the inner surface side and the outer surface side of hemispheric portion 1. Sample window 2 is an opening for attaching sample OBJ1 or standard object REF1 to the sample window, and provided at a position of substantial center of curvature O of hemispheric portion 1. In other words, sample window 2 is formed in a region including substantial center of curvature O of hemispheric portion 1. Observation window 3 is an opening for observing the illuminance on the inner surface of hemispheric portion 1, and provided at a position separated from sample window 2 toward the outer circumference side by a predetermined distance. Light is directed to spectrometer 6 through observation window 3.

Light source 7 includes a lamp 7a, a collective optical system 7b and a wavelength control optical system 7c. A xenon discharge lamp (Xe lamp) or the like is typically used as lamp 7a. Collective optical system 7b directs the light generated from lamp 7a in such a manner as to concentrate the light on sample OBJ1 or standard object REF1. In other words, collective optical system 7b narrows the optical path of excitation light L1 so that excitation light L1 entirely falls within the sample OBJ1 or standard object REF1. Wavelength control optical system 7c controls the wavelength component of excitation light L1. Wavelength control optical system 7c is typically disposed between lamp 7a and collective optical system 7b, and an optical interference filter (wavelength band-pass filter) or spectrometer is used as wavelength control optical system 7c.

Spectrometer 6 includes an attachment portion 6a, a fiber end 6b, a reflection portion 6c, an optical fiber 6d, and a detector 6e. Attachment portion 6a is disposed on plane mirror 5 in such a manner as to cover observation window 3. Optical fiber 6d and fiber end 6b connected to optical fiber 6d are inserted into attachment portion 6a. Reflection portion 6c is provided on a virtual line extended downward as seen on the drawing along a normal to observation window 3. Reflection portion 6c changes the direction of propagation of the light entering through observation window 3, by approximately 90°, and then directs the light to fiber end 6b.

Detector 6e detects the spectrum of the light introduced by optical fiber 6d. Detector 6e is typically configured to include a diffraction grating and a line sensor associated with the direction of diffraction of the diffraction grating, and outputs the intensity of the input light for each wavelength. In the case where sample OBJ1 is a phosphor, the measurable range of detector 6e is designed to cover both of the wavelength range of excitation light L1 applied from light source 7 and the wavelength range of the fluorescence generated from sample OBJ1 receiving excitation light L1.

<Integration Function>

Next, the integration function of quantum efficiency measurement apparatus SYS1 according to the present embodiment will be described. As shown in FIG. 3, excitation light L1 applied from light source 7 is incident on sample OBJ1 attached to sample window 2. Then, excitation light L1 is absorbed in sample OBJ1 at a ratio according to the material and shape, and a part of the energy causes fluorescence to be generated. Further, excitation light L1 that has not been absorbed by sample OBJ1 is reflected from sample OBJ1. The light including the fluorescence radiated from sample OBJ1 and excitation light L1 reflected from sample OBJ1 chiefly propagates toward the inner surface of hemispheric portion 1.

Plane mirror 5 reflects the light from sample OBJ1 that is incident on the mirror after being reflected from hemispheric portion 1, and generates a virtual image of the inner surface of hemispheric portion 1. Since plane mirror 5 is disposed to pass through the center of curvature of hemispheric portion 1 as described above, the space formed between plane mirror 5 and hemispheric portion 1 is a hemisphere having a constant curvature. Therefore, from the inner surface of hemispheric portion 1 and the virtual image generated by plane mirror 5, an illuminance distribution can be obtained that is identical to the one obtained in the case where a substantially spherical integrating sphere is used. In other words, this can be considered as if excitation light L1 is applied to two samples OBJ1 arranged symmetrically with each other in a spherical integrating sphere.

The fluorescence generated from sample OBJ1 and excitation light L1 reflected from sample OBJ1 are repeatedly reflected in the space surrounded by hemispheric portion 1 and plane mirror 5, and accordingly the illuminance on the inner surface of hemispheric portion 1 is made uniform. The uniform illuminance (spectrum) can be measured to measure the quantum efficiency of sample OBJ1.

As heretofore described, regarding quantum efficiency measurement apparatus SYS1 according to the present embodiment, the state where the space formed between plane mirror 5 and hemispheric portion 1 and the virtual image of this space generated by plane mirror 5 are integrated may be substantially regarded as a sphere. Thus, "substantial center of curvature of the hemispheric portion" is a concept including the absolute center of curvature of hemispheric portion 1 and, in addition thereto, a position near the absolute center of curvature with which an illuminance distribution substantially identical to the one obtained using a spherical integrating sphere as described above can be obtained.

A similar integration effect can also be achieved when standard object REF1 is attached to sample window 2 instead of sample OBJ1. Fluorescence is not generated from standard object REF1. Therefore, when excitation light L1 applied from light source 7 is incident on standard object REF1 attached to sample window 2, the light is reflected according to the reflectance characteristic of standard object REF1.

<Attachment of Sample and Standard Object>

Sample OBJ1 and standard object REF1 are each attached to sample window 2 provided in plane mirror 5 as described above. At this time, it is preferable to attach sample OBJ1 and standard object REF1 in such a manner that the exposed surface of sample OBJ1 or standard object REF1 substantially coincides with the surface (reflection surface 5a), located on hemispheric portion 1 side, of plane mirror 5. If the plane of the opening of observation window 3 does not substantially coincide with the exposed surface of sample OBJ1 or standard object REF1, for example, if the exposed surface of sample OBJ1 is lower than the plane of the opening of observation window 3, the fluorescence generated from sample OBJ1 receiving excitation light L1 and excitation light L1 reflected from sample OBJ1 are absorbed by the side surface of observation window 3, resulting in occurrence of a measurement error. On the contrary, if the exposed surface of sample OBJ1 protrudes from the plane of the opening of observation window 3, the protruded portion hinders interreflection of the fluorescence generated from sample OBJ1 receiving excitation light L1 and excitation light L1 reflected from sample OBJ1, in the integrating space formed by light diffuse reflection layer 1a on the inner surface of hemispheric portion 1 and reflection surface 5a of plane mirror 5.

In the configuration shown in FIG. 3, sample window 2 and observation window 3 are coplanar with plane mirror 5. Therefore, as long as the exposed surfaces of sample OBJ1 and standard object REF1 are flat, the fluorescence and the reflected light from sample OBJ1 and standard object REF1 do not directly enter the observation field of observation window 3. It is thus unnecessary to dispose baffle 304 as shown in FIG. 1. In this way, a light absorption error due to the baffle can be prevented, and the illuminance on the inner wall surface of hemispheric portion 1 can be further increased by means of the above-described "virtual image." With these two functions, the quantum efficiency can be measured with a higher accuracy.

<Principle of Measurement>

Next with reference to FIG. 4 (A) and FIG. 4 (B), a principle of measurement by quantum efficiency measurement apparatus SYS1 according to the present embodiment will be described.

When excitation light L1 is applied to sample OBJ1 that is typically a phosphor, a part of the excitation light (photons) is absorbed to be used for generating fluorescence, while the remaining part of excitation light L1 is reflected from the surface of the sample. It is supposed here that excitation light L1 has a wavelength range of $\lambda_{1L}$-$\lambda_{1H}$ and the fluorescence component generated from sample OBJ1 has a wavelength range of $\lambda_{2L}$-$\lambda_{2H}$. Generally, excitation light L1 is ultraviolet light and fluorescence is visible light. Therefore, the wavelength range $\lambda_{1L}$-$\lambda_{1H}$ and the wavelength range $\lambda_{2L}$-$\lambda_{2H}$ do not overlap each other. Thus, from the spectrum measured by spectrometer 6, respective components corresponding to these wavelength ranges can be selectively extracted to separate them from each other.

Figure 4:
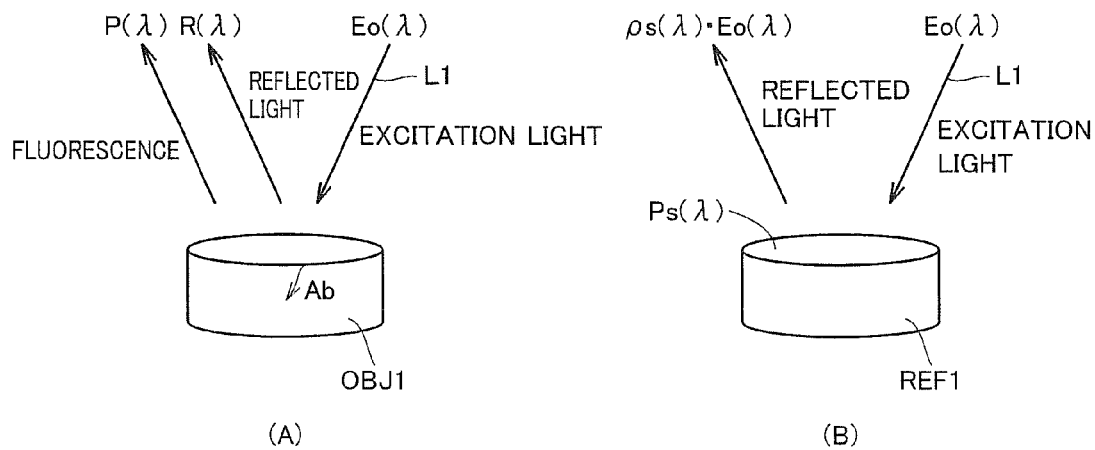
FIG. 4 is a diagram illustrating a principle of measurement by the quantum efficiency measurement apparatus according to the first embodiment of the present invention.

As shown in FIG. 4 (A), it is supposed that excitation light L1 has a spectrum $E_0(\lambda)$. Here, it is supposed that a fluorescence component is generated from sample OBJ1 as a result of application of excitation light L1 to sample OBJ1 has a spectrum $P(\lambda)$ and a reflected light component reflected from sample OBJ1 has a spectrum $R(\lambda)$. In other words, spectrum $P(\lambda)$ of the fluorescence component is equivalent to the component of the wavelength range ($\lambda_{2L}$-$\lambda_{2H}$) corresponding to the fluorescence in spectrum $E^{(1)}(\lambda)$ which is measured by spectrometer 6 when sample OBJ1 is attached, and spectrum $R(\lambda)$ of the reflected light component is equivalent to the component of the wavelength range ($\lambda_{1L}$-$\lambda_{1H}$) corresponding to excitation light L1 in spectrum $E^{(1)}(\lambda)$ which is measured by spectrometer 6.

Further, as shown in FIG. 4 (B), it is supposed that standard object REF1 has a reflectance characteristic $\rho_S(\lambda)$. Then, the spectrum measured when excitation light L1 having spectrum $E_0(\lambda)$ is applied to standard object REF1 is represented as $E^{(2)}(\lambda)=\rho_S(\lambda)\cdot E_0(\lambda)$. From this expression, spectrum $E_0(\lambda)$ of excitation light L1 can be represented by expression (1).

$$E_0(\lambda)=E^{(2)}(\lambda)/\rho_S(\lambda) \quad (1)$$

Further, as shown in FIG. 4 (A), the remaining component (photons) obtained by subtracting spectrum $R(\lambda)$ of the reflected light component reflected from sample OBJ1, from spectrum $E_0(\lambda)$ of excitation light L1, can be regarded as being absorbed by sample OBJ1.

Therefore, in order to convert the spectrum (radiation power) into the number of photons, the spectrum is divided by $hc/\lambda$ (where h: Planck's constant, c: light velocity). Then, the number of photons Ab absorbed by sample OBJ1 can be represented by expression (2) where k=1/hc.

$$Ab = k \cdot \int_{\lambda_{1L}}^{\lambda_{1H}} \lambda \cdot \left\{ \frac{E^{(2)}(\lambda)}{\rho_S(\lambda)} - E^{(1)}(\lambda) \right\} \delta\lambda \quad (2)$$

The number of photons Pph of the fluorescence can be represented by expression (3).

$$Pph = k \int_{\lambda_{2L}}^{\lambda_{2H}} \lambda \cdot E^{(1)}(\lambda) \delta\lambda \quad (3)$$

Accordingly, the internal quantum efficiency QEin of sample OBJ1 can be represented by expression (4).

$$QEin = Pph/Ab \quad (4)$$

<Control Configuration>

Next with reference to FIG. 5, a control configuration of processor 200 of quantum efficiency measurement apparatus SYS1 according to the present embodiment will be described.

Figure 5:
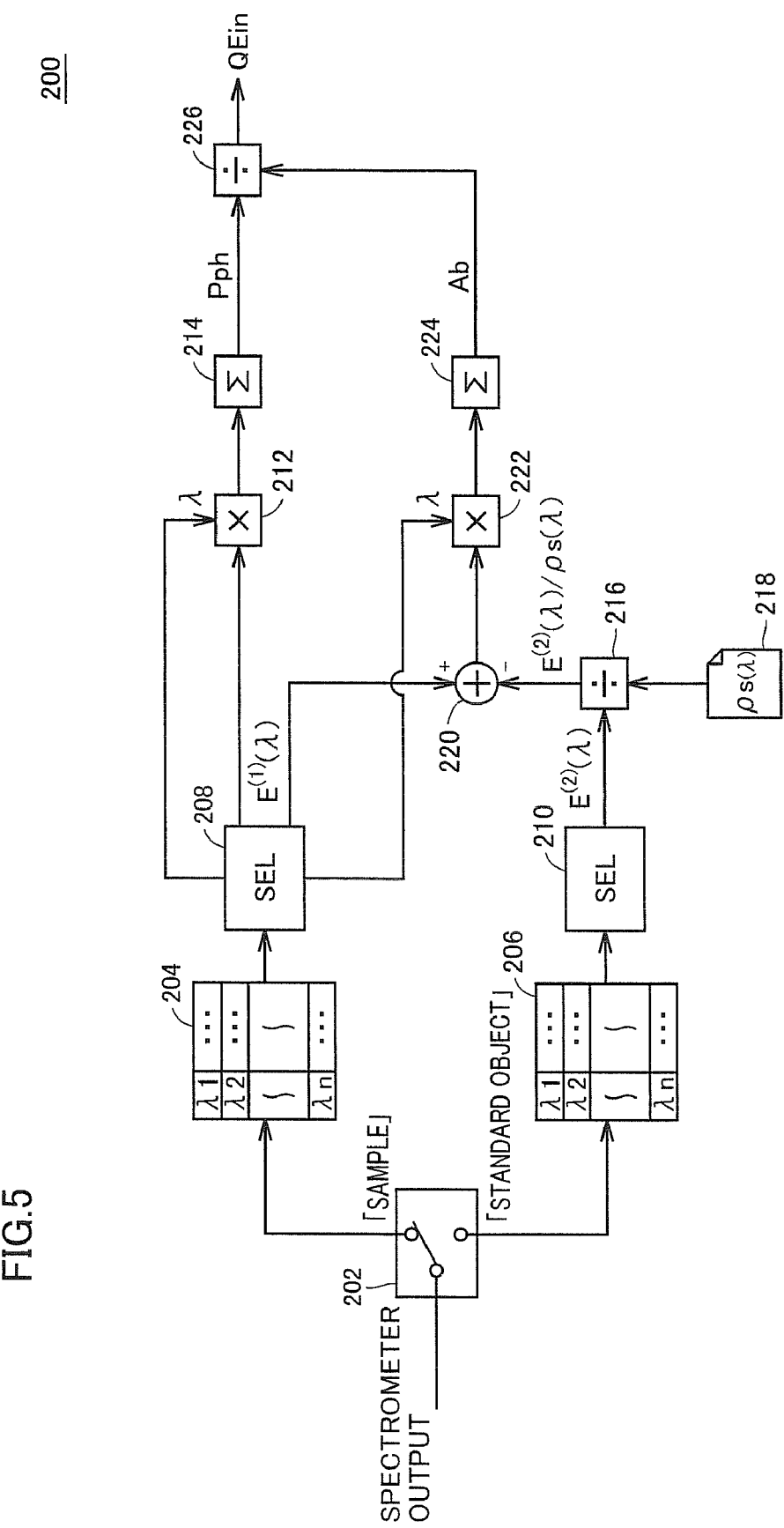
FIG. 5 is a diagram showing a control configuration of a processor of the quantum efficiency measurement apparatus according to the first embodiment of the present invention.

As shown in FIG. 5, the control configuration of processor 200 includes a switch unit 202, buffers 204, 206, selection units (SEL) 208, 210, division units 216, 226, an initial setting holding unit 218, an addition and subtraction unit 220, multiplication units 212, 222, and integration units 214, 224.

Switch unit 202 switches the storage where an output (detected spectrum) of spectrometer 6 is to be stored, to one of buffers 204 and 206, following a signal that is input according to the state of attachment to sample window 2. Specifically, when sample OBJ1 is attached to sample window 2, switch unit 202 stores spectrum $E^{(1)}(\lambda)$ detected by spectrometer 6 in buffer 204 and, when standard object REF1 is attached to sample window 2, switch unit 202 stores spectrum $E^{(2)}(\lambda)$ detected by spectrometer 6 in buffer 206.

Buffers 204 and 206 are memories for storing the spectrums detected by spectrometer 6, and have regions according to the wavelength resolution of spectrometer 6. Specifically, in the case where spectrometer 6 outputs a spectrum composed of n wavelengths in total, namely wavelengths $\lambda 1$, $\lambda 2$, ..., $\lambda n$, the buffer has respective areas for storing respective intensities for n wavelengths.

Selection units 208 and 210 selectively read wavelength components of the spectrums stored in buffers 204 and 206, respectively. From the wavelength components of read spectrum $E^{(1)}(\lambda)$, selection unit 208 outputs a component included in the wavelength range $\lambda_{1L}$-$\lambda_{1H}$ of excitation light L1 to multiplication unit 222, and outputs a component included in the wavelength range $\lambda_{2L}$-$\lambda_{2H}$ of the fluorescence component generated from sample OBJ1 to multiplication unit 212. Selection unit 208 further outputs the value of wavelength $\lambda$ of the read wavelength component to multiplication units 212 and 222.

Multiplication unit 212 and integration unit 214 perform a computation corresponding to expression (3) as described above to calculate the number of photons Pph of the fluorescence. Specifically, multiplication unit 212 multiplies the wavelength component of spectrum $E^{(1)}(\lambda)$ read by selection unit 208 by the wavelength $\lambda$ itself. Multiplication unit 212 then outputs the value of the product to integration unit 214. Integration unit 214 calculates the sum of values that are output from multiplication unit 212. As described above, wavelength components included in spectrum $E^{(1)}(\lambda)$ that correspond to the wavelength range $\lambda_{2L}$-$\lambda_{2H}$ of the fluorescence component are output to multiplication unit 212. Therefore, a computation corresponding to above-described expression (3) is substantially performed for each wavelength.

Division unit 216, addition and subtraction unit 220, multiplication unit 222, and integration unit 224 perform a computation corresponding to above-described expression (2) to calculate the number of photons Ab absorbed by sample OBJ1. Specifically, division unit 216 divides the wavelength component of spectrum $E^{(2)}(\lambda)$ read by selection unit 210 by a component of corresponding wavelength in reflectance characteristic $\rho_S(\lambda)$ of standard object REF1 stored in initial setting holding unit 218. Division unit 216 outputs the quotient $(E^{(2)}(\lambda)/\rho_S(\lambda))$ to addition and subtraction unit 220. Addition and subtraction unit 220 subtracts the quotient calculated by division unit 216 from the wavelength component of spectrum $E^{(2)}(\lambda)$ read by selection unit 208. Addition and subtraction unit 220 then outputs the calculated value to multiplication unit 222. Multiplication unit 222 multiplies the value calculated by addition and subtraction unit 220 by the corresponding wavelength $\lambda$. Multiplication unit 222 then outputs the value of the product to integration unit 224. Integration unit 224 calculates the sum of values that are output from multiplication unit 222. As described above, wavelength components included in spectrum $E^{(1)}(\lambda)$ that correspond to the wavelength range $\lambda_{1L}$-$\lambda_{1H}$ of excitation light L1 are output to multiplication unit 222, and thus a computation corresponding to above-described expression (2) is substantially performed for each wavelength.

Division unit 226 divides the number of photons Pph of the fluorescence that is calculated by integration unit 214 by the number of photons Ab absorbed by sample OBJ1 that is calculated by integration unit 224. Division unit 226 then outputs the quotient (Pph/Ab) as internal quantum efficiency QEin of sample OBJ1.

<Process Procedure>

Figure 6:
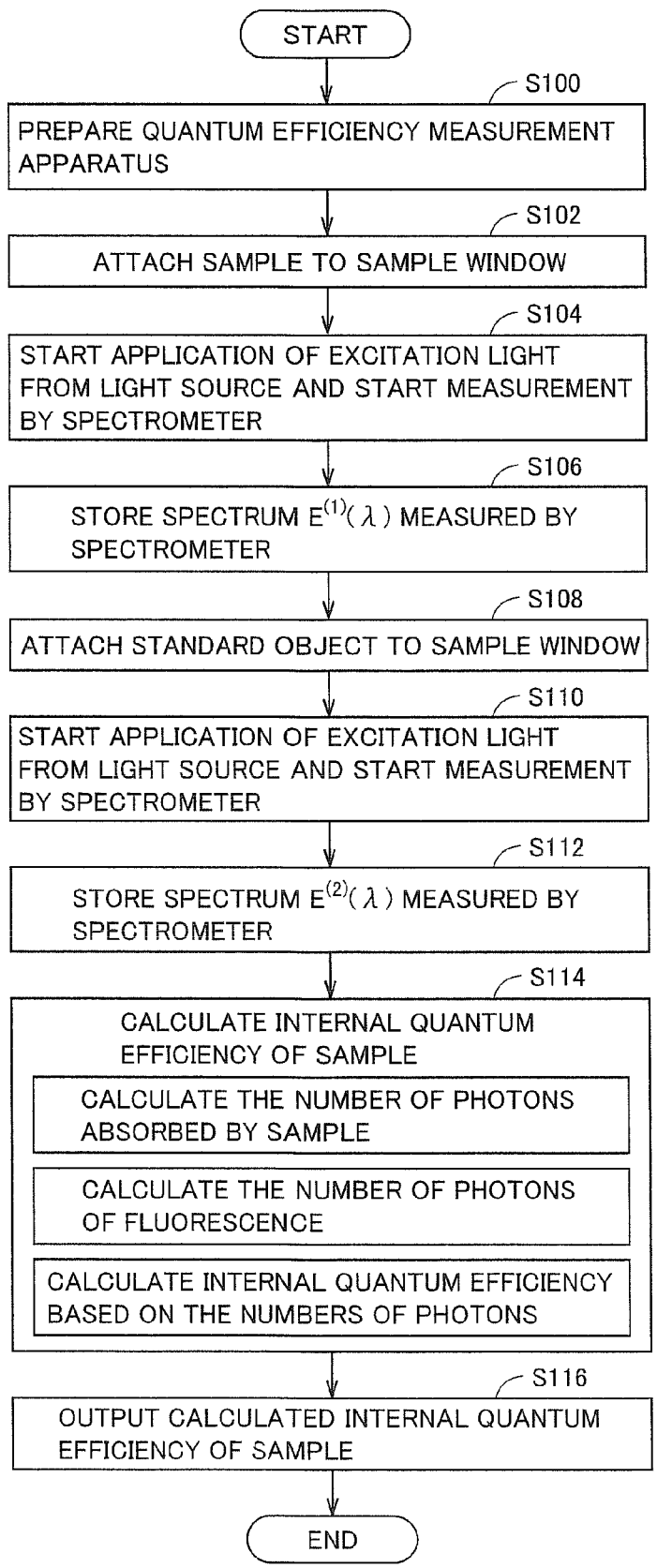
FIG. 6 is a flowchart showing a process procedure for measurement of the quantum efficiency using the quantum efficiency measurement apparatus according to the first embodiment of the present invention.

Referring next to FIG. 6, FIG. 6 is a flowchart showing a process procedure for measurement of the quantum efficiency using quantum efficiency measurement apparatus SYS1 according to the present embodiment.

A user prepares quantum efficiency measurement apparatus SYS1 (step S100). The user then attaches sample OBJ1 to sample window 2 (step S102), and causes light source 7 to start applying excitation light L1 and causes spectrometer 6 to start taking a measurement (step S104). At this time, the user may input, to processor 200, the fact that sample OBJ1 is attached to sample window 2. Accordingly, processor 200 stores spectrum $E^{(1)}(\lambda)$ measured by spectrometer 6 (step S106).

Then, the user attaches standard object REF1 to sample window 2 (step S108), and causes light source 7 to start applying excitation light L1 and causes spectrometer 6 to start taking a measurement (step S110). At this time, the user may input, to processor 200, the fact that standard object REF1 is attached to sample window 2. Accordingly, processor 200 stores spectrum $E^{(2)}(\lambda)$ measured by spectrometer 6 (step S112).

After spectrum $E^{(1)}(\lambda)$ and spectrum $E^{(2)}(\lambda)$ have been obtained, processor 200 calculates internal quantum efficiency QEin of sample OBJ1 based on these spectrums (step S114). More specifically, based on the wavelength components corresponding to the wavelength range $\lambda_{1L}$-$\lambda_{1H}$ of spectrum $E^{(1)}(\lambda)$, the wavelength components of spectrum $E^{(2)}(\lambda)$ and reflectance characteristic $\rho_S(\lambda)$ of standard object REF1, processor 200 calculates the number of photons Ab absorbed by sample OBJ1. Further, based on the wavelength components corresponding to the wavelength range $\lambda_{2L}$-$\lambda_{2H}$ of spectrum $E^{(1)}(\lambda)$, processor 200 calculates the number of photons Pph of the fluorescence. Processor 200 further calculates internal quantum efficiency QEin of sample OBJ1 based on the number of photons Ab and the number of photons Pph.

Processor 200 further outputs the calculated internal quantum efficiency QEin of sample OBJ1 (step S116). Here, examples of the output of internal quantum efficiency QEin may include indication of internal quantum efficiency QEin on a monitor or the like, print output of internal quantum efficiency QEin and storage of internal quantum efficiency QEin on a recording medium, for example.

While the flowchart shown in FIG. 6 illustrates an example of a measurement procedure where spectrum $E^{(1)}(\lambda)$ for sample OBJ1 is obtained first and subsequently spectrum $E^{(2)}(\lambda)$ for standard object REF1 is obtained, the procedure does not limited to the illustrated procedure as long as spectrum $E^{(1)}(\lambda)$ and spectrum $E^{(2)}(\lambda)$ can be obtained. For example, after spectrum $E^{(2)}(\lambda)$ for standard object REF1 is obtained, spectrum $E^{(1)}(\lambda)$ for sample OBJ1 may be obtained. In this case, spectrum $E^{(2)}(\lambda)$ obtained for standard object REF1 is used to successively obtain spectrum $E^{(1)}(\lambda)$ for each of a plurality of samples OBJ1 so that internal quantum efficiency QEin of a plurality of samples OBJ1 can be efficiently calculated. In other words, after standard object REF1 is attached to sample window 2 to obtain spectrum $E^{(2)}(\lambda)$, a plurality of samples OBJ1 may be attached one after another to sample window 2.

Effects of the Present Embodiment

The present embodiment does not require a baffle to be provided in the integrating hemisphere for the purpose of preventing direct incidence of light from a sample and therefore, can reduce occurrence of a measurement error due to light absorption by the baffle. Further, the present embodiment uses a virtual image generated by the plane mirror so that a twofold light intensity can be obtained in principle as compared with the case where an integrating sphere of the same radius is used. The quantum efficiency can thus be measured with a higher accuracy.

Further, since the present embodiment can achieve a twofold light intensity in principle, it is unnecessary to excessively decrease the radius of the hemispheric portion for the purpose of enhancing the measurement accuracy. Accordingly, the opening area of the observation window can be made relatively small with respect to the inner surface area of the integrating hemisphere, so that occurrence of a measurement error due to the observation window can be reduced.

First Modification of the First Embodiment

Figure 7:
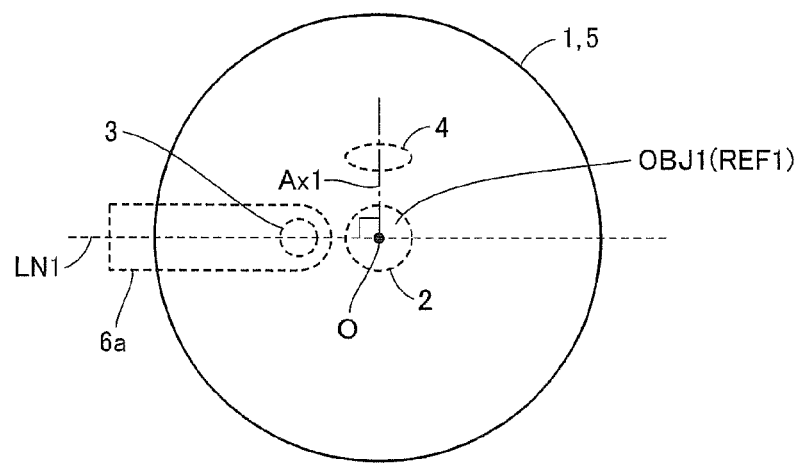
FIG. 7 is a plan view showing a positional relation between a spectrometer and a light source of a quantum efficiency measurement apparatus according to a first modification of the first embodiment of the present invention.

While the above-described first embodiment does not particularly limit the positional relation between spectrometer 6 and light source 7, it is preferable to arrange spectrometer 6 and light source 7 with the positional relation as shown in FIG. 7.

As shown in the plan view of FIG. 7 where integrating hemisphere 100 is seen from hemispheric portion 1 side, a first modification of the first embodiment arranges attachment portion 6a of spectrometer 6 to extend in the direction of a normal LN1 orthogonal to optical axis Ax1 of excitation light L1 applied from light source 7. The arrangement of spectrometer 6 and light source 7 with this positional relation can prevent excitation light L1 applied to a sample OBJ1 from directly entering spectrometer 6.

Second Modification of the First Embodiment

In quantum efficiency measurement apparatus SYS1 according to the first embodiment as described above, preferably a light transmission diffusion member is disposed on the light propagation path of observation window 3. In the following, a quantum efficiency measurement apparatus SYS1A according to a second modification of the present embodiment will be described with reference to FIG. 8.

Figure 8:
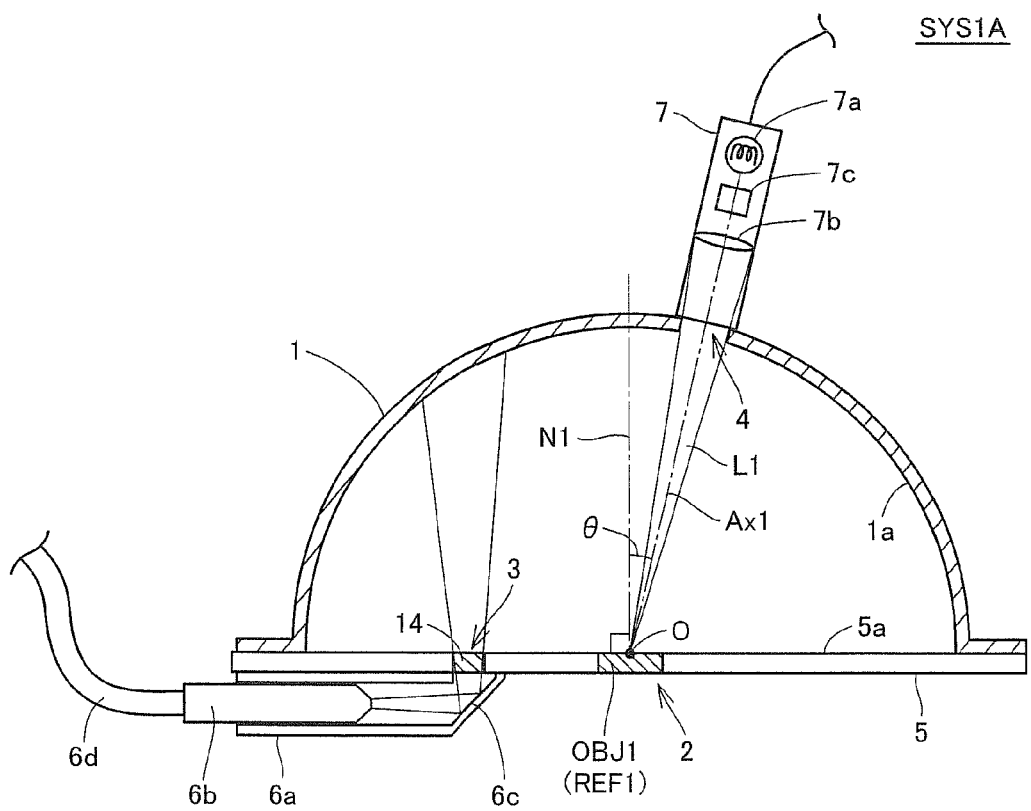
FIG. 8 is a cross section showing main components of a quantum efficiency measurement apparatus according to a second modification of the first embodiment of the present invention.

Quantum efficiency measurement apparatus SYS1A shown in FIG. 8 additionally includes a light transmission diffusion member 14 provided to observation window 3 as compared with quantum efficiency measurement apparatus SYS1 according to the first embodiment shown in FIG. 3. Specifically, light transmission diffusion member 14 is disposed between the inside of hemispheric portion 1 and spectrometer 6. Other components are similar to those shown in FIG. 3, and the detailed description thereof will not be repeated.

Light transmission diffusion member 14 diffuses the light in integrating hemisphere 100 and then guides the light to spectrometer 6. Therefore, even if the observation field of observation window 3 is relatively small, the influence of unevenness of the reflectance or the like on light diffuse reflection layer 1a provided on the inner surface of hemispheric portion 1 can be reduced. In other words, if light transmission diffusion member 14 is not provided, only the illuminance on a part of the inner surface of hemispheric portion 1, the part corresponding to the observation field of observation window 3, is observed. Thus, if there is unevenness of the reflectance or the like on the part corresponding to the observation field, the result of the measurement is likely to be influenced by the unevenness. In contrast, in the case where light transmission diffusion member 14 is provided, the light present around observation window 3 is diffused and then directed to spectrometer 6, so that the above-described problem can be avoided.

Second Embodiment

In connection with the above-described first embodiment, quantum efficiency measurement apparatus SYS1 where a sample is attached to the sample window provided in the plane mirror is illustrated. In connection with a second embodiment, a configuration will be illustrated where a sample is attached to a sample window provided in the hemispheric portion.

Figure 9:
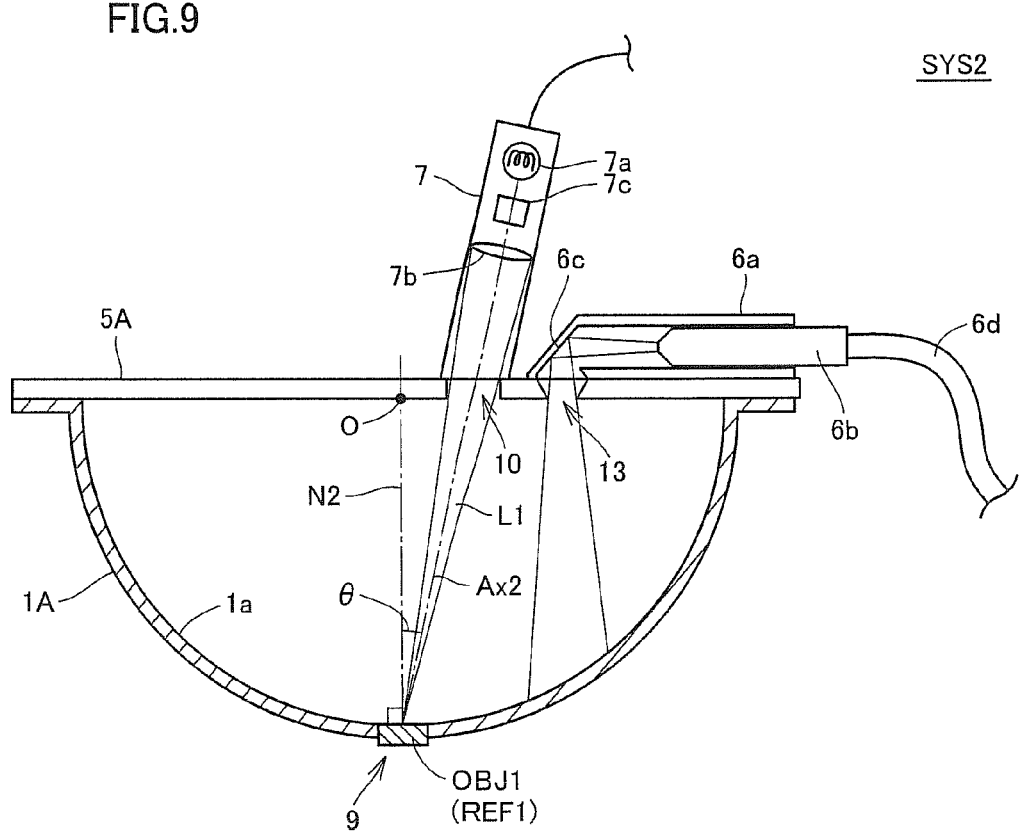
FIG. 9 is a cross section showing main components of a quantum efficiency measurement apparatus according to a second embodiment of the present invention.

The appearance of a quantum efficiency measurement apparatus SYS2 according to the second embodiment of the present invention is similar to that in FIG. 2 as described above, and the detailed description thereof will not be repeated. Referring to FIG. 9, an integrating hemisphere of quantum efficiency measurement apparatus SYS2 further includes a hemispheric portion 1A, a disk-shaped plane mirror 5A disposed to close an opening of hemispheric portion 1A, a spectrometer 6 for measuring the illuminance (light spectrum) on the inner wall surface of hemispheric portion 1A, and a light source 7 generating excitation light L1.

Hemispheric portion 1A is similar to hemispheric portion 1 shown in FIG. 3 except that the former includes a sample window 9 for attaching thereto a sample OBJ1 and a standard object REF1. Sample window 9 is provided at the position where a normal N2 to plane mirror 5A that passes through a substantial center of curvature O of hemispheric portion 1A intersects with hemispheric portion 1A. Namely, sample window 9 is provided at the position of the apex of the hemisphere surrounded by hemispheric portion 1A and plane mirror 5A. Regarding sample OBJ1 and standard object REF1 as well, the present embodiment is similar to the above-described first embodiment, and the detailed description thereof will not be repeated.

In plane mirror 5A, a light source window 10 and an observation window 13 that are each able to communicate with the inner surface side and the outer surface side of hemispheric portion 1A are provided.

Light source window 10 is provided in the vicinity of substantial center of curvature O of hemispheric portion 1A. More specifically, light source window 10 is provided at the position where excitation light L1 is applied toward sample window 9 at angle θ with respect to normal N2 to plane mirror 5. Namely, light source 7 applies excitation light L1, along an optical axis Ax2 having angle θ with respect to normal N2 to plane mirror 5A, toward sample OBJ1 or standard object REF1 attached to sample window 9.

Observation window 13 is an opening for observing the illuminance on the inner surface of hemispheric portion 1A, and provided at a position separated from light source window 10 toward the outer circumference side by a predetermined distance. Through observation window 13, light is directed to spectrometer 6. Observation window 13 restrains fluorescence generated from sample OBJ1 receiving excitation light L1 as well as excitation light L1 reflected from sample OBJ1 from directly entering spectrometer 6. More specifically, observation window 13 is a kind of aperture, namely an opening configured in such a manner that the diameter of the opening on the outer side of hemispheric portion 1A is larger relative to the diameter of the opening on the inner side of hemispheric portion 1A. Such an observation window 13 restraining the observation field can be provided to measure the quantum efficiency with a higher accuracy without providing baffle 304 as shown in FIG. 1.

Other features of plane mirror 5A are similar to those of plane mirror 5 shown in FIG. 3, and the detailed description thereof will not be repeated. Further, regarding spectrometer 6 and light source 7 as well, the detailed description as given above will not be repeated. Spectrometer 6 and light source 7 are preferably arranged with the positional relation as shown in FIG. 7 as described above.

Further, the control configuration of processor 200 of quantum efficiency measurement apparatus SYS2 according to the present embodiment, and the flowchart showing a process procedure for measurement of the quantum efficiency using quantum efficiency measurement apparatus SYS2 according to the present embodiment are similar to those of FIGS. 5 and 6 respectively, and the detailed description thereof will not be repeated.

Effects of the Present Embodiment

The present embodiment employs the observation window where the observation field is restrained and therefore requires no baffle provided in the integrating hemisphere for preventing direct incidence of light from the sample. Thus, occurrence of a measurement error due to light absorption by the baffle can be reduced. Further, the present embodiment can achieve, by means of a virtual image generated by the plane mirror, a twofold light intensity in principle relative to the case where an integrating sphere with the same radius is used. In this way, even if the observation field of the observation window is restrained, a sufficient brightness can be achieved.

Accordingly, the quantum efficiency can be measured with a higher accuracy.

Third Embodiment

In connection with the first and second embodiments as described above, the configuration suitable for measurement of the quantum efficiency of a solid sample is mainly illustrated. In connection with a third embodiment, a configuration will be illustrated that is suitable for measurement of a liquid sample.

<Related Art>

For the sake of facilitating understanding of a quantum efficiency measurement apparatus according to the present embodiment, a quantum efficiency measurement apparatus relevant to the present embodiment will be described first with reference to FIG. 10.

Figure 10:
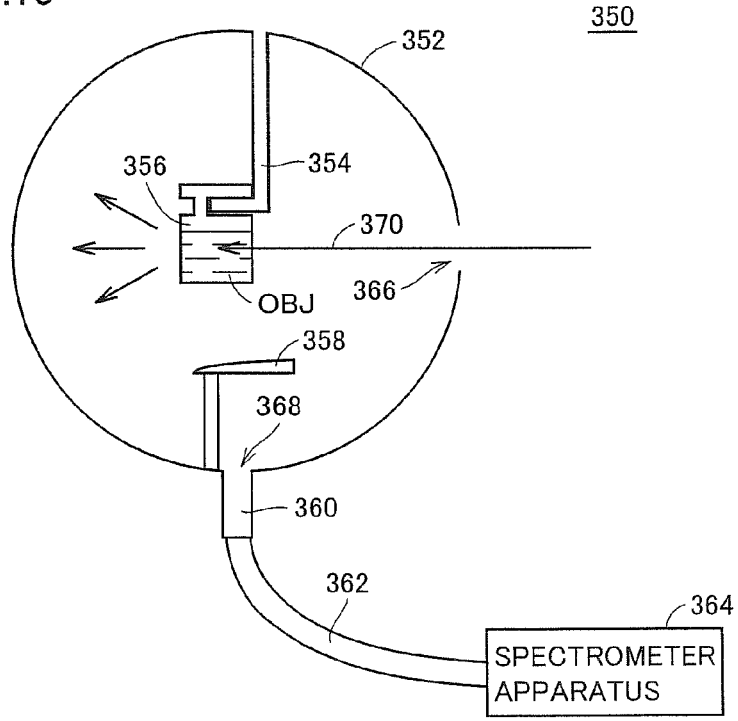
FIG. 10 is a schematic configuration diagram of a quantum efficiency measurement apparatus relevant to a third embodiment of the present invention.

Quantum efficiency measurement apparatus 350 shown in FIG. 10 that is relevant to the present embodiment chiefly measures the quantum efficiency of a liquid sample OBJ. Specifically, quantum efficiency measurement apparatus 350 includes an integrating sphere 352, a support 354, a baffle 358, a light receiving unit 360, an optical fiber 362, and a spectrometer apparatus 364. In this quantum efficiency measurement apparatus 350, a transparent container 356 enclosing a sample is hung by support 354 in integrating sphere 352, and an excitation light 370 is applied to this sample OBJ through a light source window 366 from a light source (not shown) provided outside integrating sphere 352. Sample OBJ receives excitation light 370 to emit fluorescence. The fluorescence radiated from sample OBJ is multiple-reflected from the inner surface of integrating sphere 352 to be integrated (made uniform). Light receiving unit 360 extracts, through an observation window 368 provided in integrating sphere 352, a part of the light of integrating sphere 352 to direct the extracted light via optical fiber 362 to spectrometer apparatus 364.

If the fluorescence generated from sample OBJ and excitation light 370 reflected from sample OBJ directly enter observation window 368, a measurement error occurs. Therefore, baffle 358 is provided between transparent container 356 and observation window 368.

Since support 354 and baffle 358 absorb light such as fluorescence as described above, support 354 and baffle 358 are internal structural components that are factors of a measurement error in quantum efficiency measurement apparatus 350.

<Apparatus Configuration>

Next, a quantum efficiency measurement apparatus SYS3 according to the present embodiment will be described.

Figure 11:
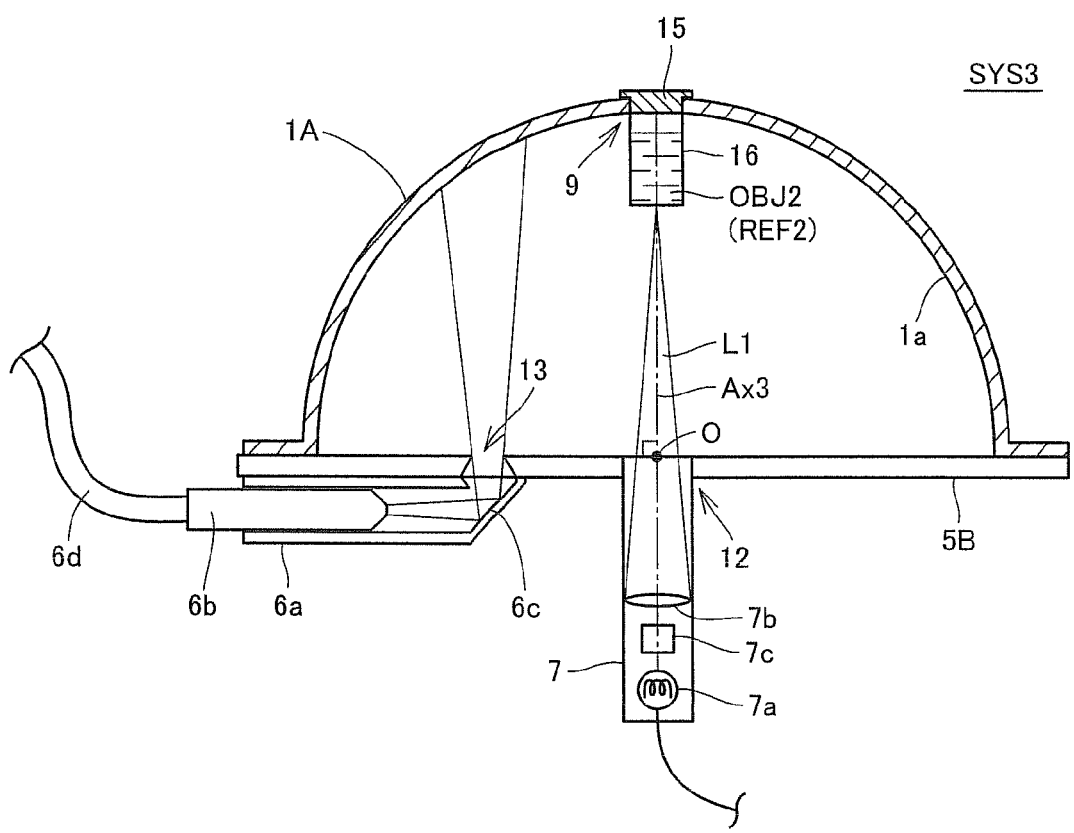
FIG. 11 is a cross section showing main components of a quantum efficiency measurement apparatus according to the third embodiment of the present invention.

The appearance of quantum efficiency measurement apparatus SYS3 according to the third embodiment of the present invention is similar to that in FIG. 2 as described above, and the detailed description thereof will not be repeated. Referring to FIG. 11, an integrating hemisphere of quantum efficiency measurement apparatus SYS3 further includes a hemispheric portion 1A, a disk-shaped plane mirror 5B disposed to close the opening of hemispheric portion 1A, a spectrometer 6 for measuring the illuminance (light spectrum) on the inner wall surface of hemispheric portion 1A, and a light source 7 generating excitation light L1.

Hemispheric portion 1A is basically identical to hemispheric portion 1A shown in FIG. 9 except that a liquid sample OBJ2 enclosed in a transparent cell 16 is attached instead of sample OBJ1. Further, a standard object REF2 corresponding to sample OBJ2 can also be attached to hemispheric portion 1A. Typically, standard object REF2 is an object that is a reference material (typically only a medium corresponding to the sample from which a phosphor is removed) of the same quantity as sample OBJ2 and enclosed in the same transparent cell 16. Standard object REF2 can be regarded as substantially emitting no fluorescence.

Plane mirror 5B is provided with a light source window 12 and an observation window 13 that are each able to communicate with the inner surface side and the outer surface side of hemispheric portion 1A.

Light source window 12 is provided at the position of a substantial center of curvature O of hemispheric portion 1A. In other words, light source window 12 is formed in a region including substantial center of curvature O of hemispheric portion 1A. Light source 7 applies excitation light L1 through light source window 12 and along an optical axis Ax3 coinciding with the normal to plane mirror 5B, toward sample OBJ2 or standard object REF2 attached to sample window 9.

Observation window 13 is an opening for observing the illuminance on the inner surface of hemispheric portion 1A, and provided at a position separated from light source window 12 toward the outer circumference side by a predetermined distance. Light 6 is directed to spectrometer 6 through observation window 13. Observation window 13 restrains fluorescence generated from sample OBJ2 receiving excitation light L1 and excitation light L1 reflected from sample OBJ2 from directly entering spectrometer 6. More specifically, observation window 13 is a kind of aperture, namely an opening configured in such a manner that the diameter of the opening on the outer side of hemispheric portion 1A is larger relative to the diameter of the opening on the inner side of hemispheric portion 1A. Such an observation window 13 restraining the observation field can be provided to measure the quantum efficiency with a higher accuracy without disposing baffle 358 as shown in FIG. 10.

Other features of plane mirror 5B are similar to those of plane mirror 5 shown in FIG. 3, and the detailed description thereof will not be repeated. Further, the detailed description of spectrometer 6 and light source 7 as described above will not be repeated.

Transparent cell 16 is a tubular container whose wall is formed of a transparent material. Transparent cell 16 is attached to sample window 9 to be disposed on optical axis Ax3 of light source 7. Thus, to sample OBJ2 enclosed in transparent cell 16, excitation light L1 is applied along optical axis Ax3. When transparent cell 16 is attached to sample window 9, the transparent cell is entirely contained in hemispheric portion 1A. At this time, a seal member 15 is attached to the outermost part of transparent cell 16. Seal member 15 prevents excitation light L1 having passed in transparent cell 16 and sample OBJ2 in the cell from leaking from hemispheric portion 1A. Therefore, at least the side of seal member 15 that faces transparent cell 16 is provided with a light diffuse reflection layer of substantially the same diffuse reflection capability as light diffuse reflection layer 1a of hemispheric portion 1A.

<Principle of Measurement>

Next, a principle of measurement by quantum efficiency measurement apparatus SYS3 according to the present embodiment will be described.

As shown in FIG. 11, when excitation light L1 is applied to sample OBJ2 that is typically a phosphor, a part of the excitation light (photons) is absorbed to be used for generating fluorescence, while the remaining part of excitation light L1 is scatter-reflected from seal member 15 for example after passing through sample OBJ2. It is supposed here that excitation light L1 has a wavelength range of $\lambda_{1L}$-$\lambda_{1H}$ and the fluorescence component generated from sample OBJ2 has a wavelength range of $\lambda_{2L}$-$\lambda_{2H}$.

It is supposed that excitation light L1 has a spectrum $E_0(\lambda)$. It is further supposed that the fluorescence component generated from sample OBJ2 by application of excitation light L1 to sample OBJ2 has a spectrum $P(\lambda)$, and the transmitted light component that is transmitted through sample OBJ2 and thereafter scatter-reflected has a spectrum $T(\lambda)$. In other words, spectrum $P(\lambda)$ of the fluorescence component is equivalent to the component of the wavelength range ($\lambda_{2L}$-$\lambda_{2H}$) corresponding to the fluorescence in spectrum $E^{(1)}(\lambda)$ measured by spectrometer 6 when sample OBJ2 is attached, and spectrum $T(\lambda)$ of the transmitted light component is equivalent to the component of the wavelength range ($\lambda_{1L}$-$\lambda_{1H}$) corresponding to excitation light L1 in spectrum $E^{(1)}(\lambda)$.

Further, spectrum $E^{(2)}(\lambda)$ measured by spectrometer 6 when standard object REF2 is attached corresponds to the radiation power that can be used for generating fluorescence in standard object REF1 out of applied light.

Therefore, in order to convert the spectrum (radiation power) into the number of photons, the spectrum is divided by hc/X (where h: Planck's constant, c: light velocity). Then, the number of photons Ab absorbed by sample OBJ2 can be represented by expression (5) where k=1/hc.

$$Ab = k \cdot \int_{\lambda_{1L}}^{\lambda_{1H}} \lambda \cdot \{E^{(2)}(\lambda) - E^{(1)}(\lambda)\} \delta\lambda \quad (5)$$

The number of photons Pph of the fluorescence can be represented by expression (6).

$$Pph = k \cdot \int_{\lambda_{2L}}^{\lambda_{2H}} \lambda \cdot E^{(1)}(\lambda) \delta\lambda \quad (6)$$

Accordingly, the internal quantum efficiency QEin of sample OBJ2 can be represented by expression (7).

$$QEin = Pph/Ab \quad (7)$$

<Control Configuration>

Figure 12:
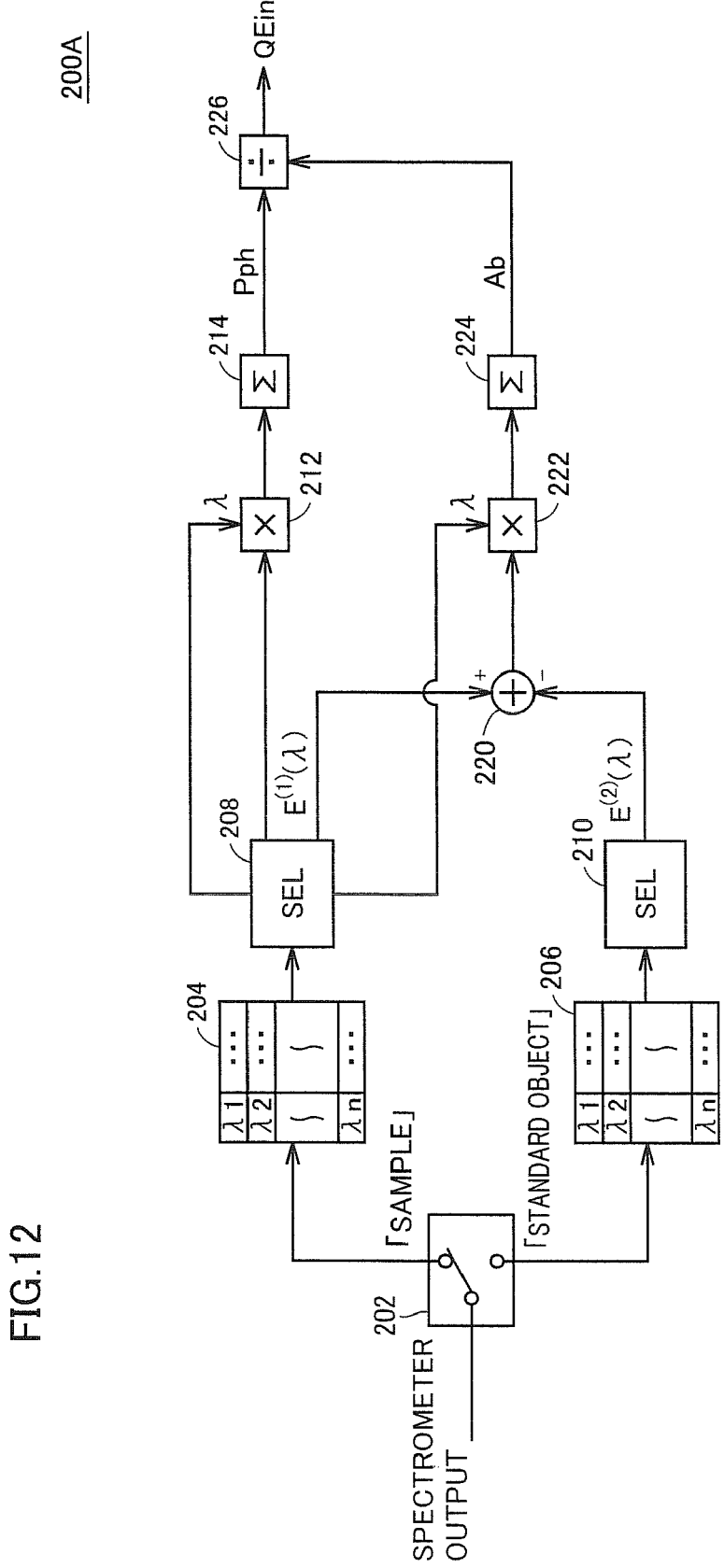
FIG. 12 is a diagram showing a control configuration of a processor of the quantum efficiency measurement apparatus according to the third embodiment of the present invention.

Referring next to FIG. 12, a control configuration of a processor 200A of quantum efficiency measurement apparatus SYS3 according to the present embodiment will be described.

As compared with the control configuration of processor 200 according to the first embodiment shown in FIG. 5, processor 200A shown in FIG. 12 does not include division unit 216 and initial setting holding unit 218, but outputs to addition and subtraction unit 220 a wavelength component of spectrum $E^{(2)}(\lambda)$ read by selection unit 210. Namely, according to expression (5) above, the number of photons Ab absorbed by sample OBJ2 is calculated.

Other components are similar to those of processor 200 shown in FIG. 5, and the detailed description thereof will not be repeated.

<Process Procedure>

A flowchart showing a process procedure for measurement of the quantum efficiency using quantum efficiency measurement apparatus SYS3 according to the present embodiment is similar to that of FIG. 6 except for the expression for calculating the number of photons Ab, and the detailed description thereof will not be repeated.

Effects of the Present Embodiment

The present embodiment employs the observation window where the observation field is restrained, and therefore does not require a baffle to be provided in the integrating hemisphere for preventing direct incidence of light from the sample. Thus, occurrence of a measurement error due to light absorption by the baffle can be reduced. Further, the present embodiment can achieve a twofold light intensity in principle, by means of a virtual image generated by the plane mirror, relative to the case where an integrating sphere of the same radius is used. In this way, even if the observation field of the observation window is restrained, a sufficient brightness can be obtained.

Accordingly, the quantum efficiency can be measured with a higher accuracy.

First Modification of the Third Embodiment

In connection with the above-described third embodiment, the configuration is illustrated where excitation light L1 is applied from light source window 12 provided in hemispheric portion 1 toward the sample attached in hemispheric portion 1. Alternatively, the light source and the sample may be arranged close to each other. In the following, with reference to FIG. 13, a quantum efficiency measurement apparatus SYS3A according to a first modification of the present embodiment will be described.

Figure 13:
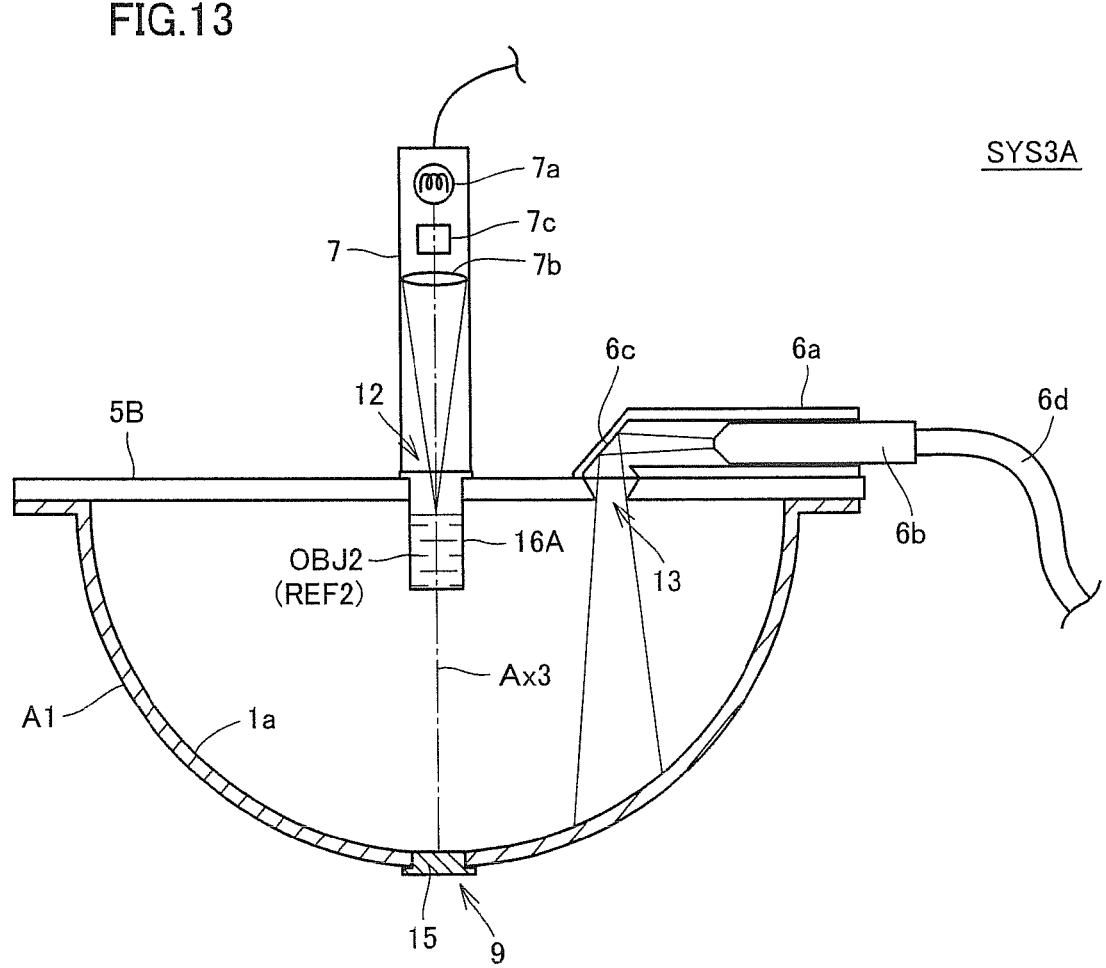
FIG. 13 is a cross section showing main components of a quantum efficiency measurement apparatus according to a first modification of the third embodiment of the present invention.

Quantum efficiency measurement apparatus SYS3A shown in FIG. 13 differs from quantum efficiency measurement apparatus SYS3 according to the third embodiment shown in FIG. 11 in that a transparent cell 16A enclosing a liquid sample OBJ2 and a light source 7 are attached to a light source window 12, and only a seal member 15 is attached to a sample window 9.

Transparent cell 16A is a tubular container entirely formed of a transparent material. Transparent cell 16A is attached to face the emission opening of light source 7 to be disposed on an optical axis Ax3 of light source 7. Light source 7 applies excitation light L1 through light source window 12 along optical axis Ax3 coinciding with the normal to plane mirror 5B, toward sample OBJ2 (or standard object REF2) attached to light source window 12. Accordingly, excitation light L1 is applied along optical axis Ax3 to sample OBJ2 enclosed in transparent cell 16A. When transparent cell 16A is attached to light source window 12, the transparent cell is entirely contained in hemispheric portion 1A.

Other features are similar to those of FIG. 11 except for the above-described positional relation between transparent cell 16A and light source 7, and the detailed description thereof will not be repeated.

Further, the control configuration of the processor of quantum efficiency measurement apparatus SYS3A according to the first modification as well as the flowchart showing the process procedure for measuring the quantum efficiency using quantum efficiency measurement apparatus SYS3A according to the first modification are respectively similar to those of FIGS. 12 and 6, and the detailed description thereof will not be repeated.

The first modification can further shorten the distance between the light source and the sample, so that a more intense excitation light can be applied to the sample. Thus, the intensity of the fluorescence generated from the sample can be further increased, so that the quantum efficiency can be measured with a higher accuracy.

Second Modification of the Third Embodiment

In connection with the third embodiment as described above, the configuration is illustrated where the transparent cell enclosing the sample is entirely contained in the hemispheric portion. As long as the excitation light can be applied to the transparent cell (sample), however, the transparent cell enclosing the sample may not entirely be contained in the hemispheric portion. In the following, with reference to FIG. 14, a quantum efficiency measurement apparatus SYS3B according to a second modification of the present embodiment will be described.

Figure 14:
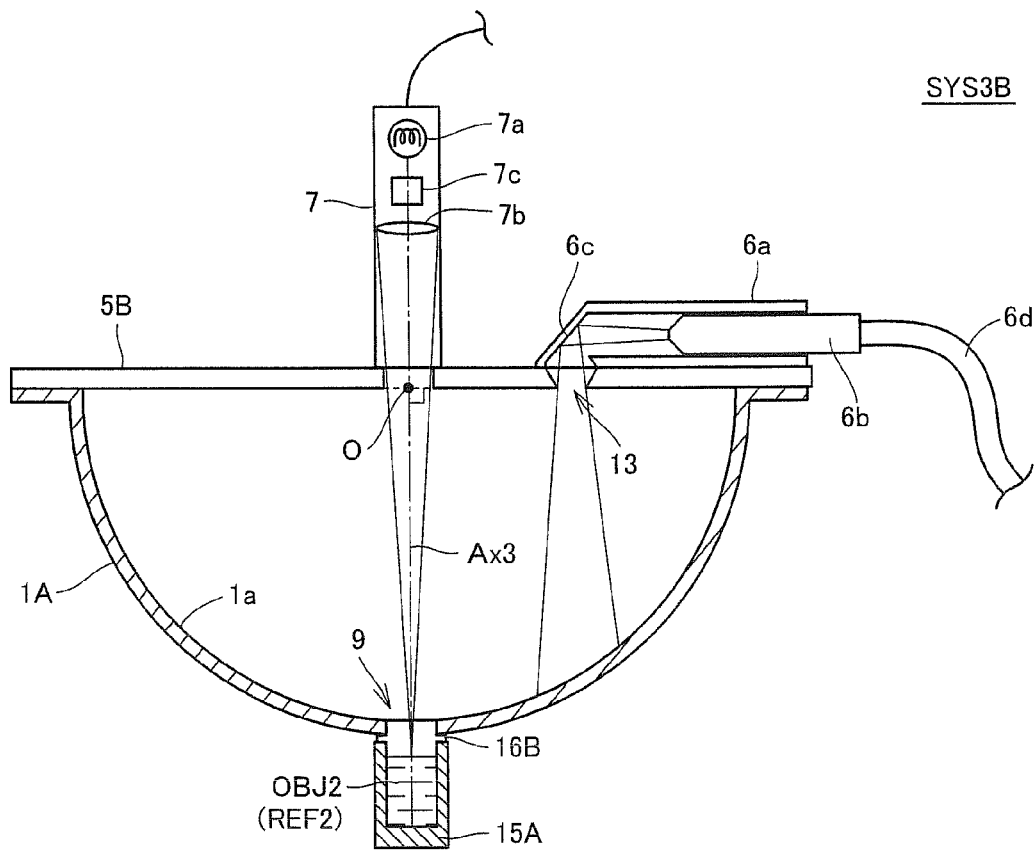
FIG. 14 is a cross section showing main components of a quantum efficiency measurement apparatus according to a second modification of the third embodiment of the present invention.

Quantum efficiency measurement apparatus SYS3B shown in FIG. 14 substantially corresponds to quantum efficiency measurement apparatus SYS3 of the third embodiment shown in FIG. 11 in which the shape of the transparent cell attached to sample window 9 is changed. Preferably, sample window 9 is disposed on the lower side relative to the direction of gravity in quantum efficiency measurement apparatus SYS3B as shown in FIG. 14.

More specifically, to sample window 9 of quantum efficiency measurement apparatus SYS3B, a transparent cell 16B enclosing a liquid sample OBJ2 and a seal member 15A are attached. Transparent cell 16B is basically a tubular container entirely formed of a transparent material. Transparent cell 16B is attached to sample window 9 to be disposed on optical axis Ax3 of light source 7. Namely, to sample OBJ2 enclosed in transparent cell 16B, excitation light L1 is applied along optical axis Ax3. At this time, a tubular seal member 15A is attached to a surface of transparent cell 16B, except for the surface of transparent cell 16B on which excitation light L1 is incident. This seal member 15A prevents excitation light L1 after passing through transparent cell 16B and sample OBJ2 therein from leaking from hemispheric portion 1A. Therefore, the inner circumference surface of seal member 15A is provided with a light diffuse reflection layer of substantially the same degree of light diffuse reflection capability as light diffuse reflection layer 1a of hemispheric portion 1A.

Other components are similar to those of FIG. 11 except for transparent cell 16B and seal member 15A, and the detailed description thereof will not be repeated.

Further, the control configuration of the processor of quantum efficiency measurement apparatus SYS3B according to the present second modification as well as the flowchart showing the process procedure for measuring the quantum efficiency using quantum efficiency measurement apparatus SYS3B according to the present second modification are respectively similar to those of FIGS. 12 and 6, and the detailed description thereof will not be repeated.

The second modification does not require that the sample and the standard object be contained in the integrating hemisphere, so that the sample and the standard object can be attached in a shorter time. Therefore, measurement can be performed more efficiently.

Fourth Embodiment

Figure 15:
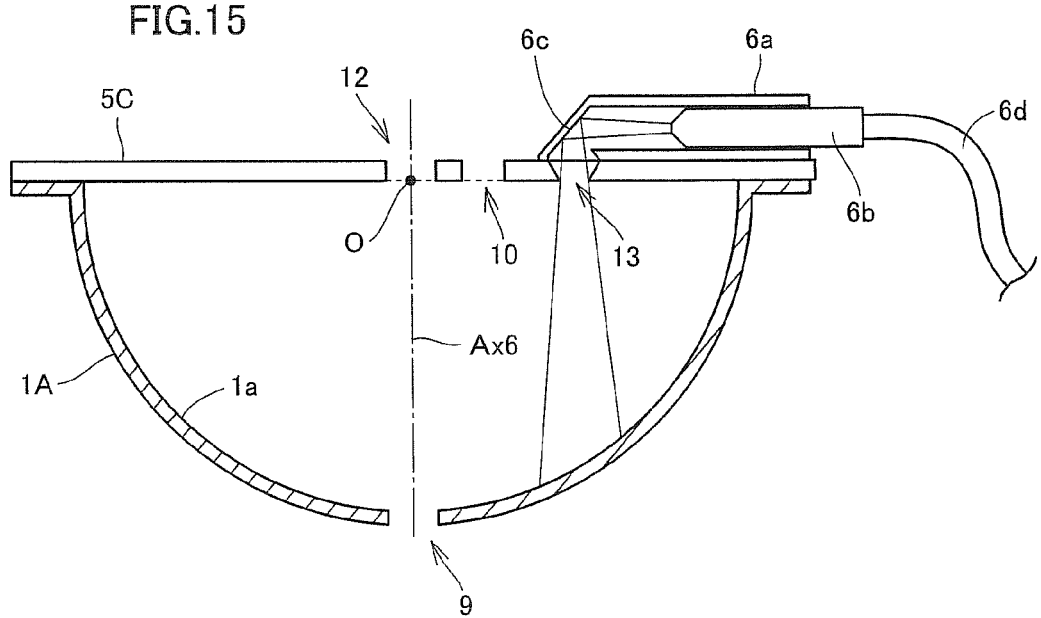
FIG. 15 is a cross section showing main components of a quantum efficiency measurement apparatus according to a fourth embodiment of the present invention.

In order to implement, as required, any of respective configurations of the quantum efficiency measurement apparatuses described in connection with the second embodiment, the third embodiment and the modifications of the third embodiment, an integrating hemisphere as shown in FIG. 15 may be employed.

Referring to FIG. 15, the integrating hemisphere of a quantum efficiency measurement apparatus according to the fourth embodiment of the present invention includes a hemispheric portion 1A and a disk-shaped plane mirror 5C disposed to close the opening of hemispheric portion 1A. In plane mirror 5C, light source windows 10 and 12 and an observation window 13 that are each able to communicate with the inner surface side and the outer surface side of hemispheric portion 1A are provided. Light source window 10 is provided for implementing quantum efficiency measurement apparatus SYS2 of the second embodiment shown in FIG. 9. Light source window 12 is provided for implementing quantum efficiency measurement apparatuses SYS3, SYS3A and SYS3B of the third embodiment and the modifications of the third embodiment shown in FIGS. 11, 13 and 14 respectively.

To any of light source windows 10 and 12 and observation window 13, components such as sample OBJ2 and light source are attached as required, and a corresponding seal member is attached to the window that is not used, so that any of the above-described quantum efficiency measurement apparatuses can be implemented as desired by the user.

The present embodiment can use a common integrating hemisphere to measure the quantum efficiency with an apparatus configuration as desired by the user.

Other Embodiments

Using any of the above-described quantum efficiency measurement apparatuses, the reflectance characteristic of a sample can be measured as well.

It should be construed that embodiments disclosed herein are by way of illustration in all respects, not by way of limitation. It is intended that the scope of the present invention is defined by claims, not by the above description, and includes all modifications and variations equivalent in meaning and scope to the claims.

The invention claimed is:

1. A quantum efficiency measurement apparatus comprising:
   a hemispheric portion with an inner surface having a light diffuse reflection layer;
   a plane mirror disposed to pass through a substantial center of curvature of said hemispheric portion and close an opening of said hemispheric portion, said plane minor including a first window provided at a position of the substantial center of curvature of said hemispheric portion for attaching an object to be measured to the first window, and a second window provided at a position apart by a predetermined distance from said first window;
   a spectrometer for measuring a spectrum in said hemispheric portion through said second window;
   a light source for applying an excitation light, through a third window provided in said hemispheric portion, at a predetermined angle with respect to a normal to said plane mirror toward said first window; and
   a processor for calculating a quantum efficiency of said object to be measured, based on a first spectrum measured by said spectrometer in a case where said object to be measured is disposed at said first window, and a second spectrum measured by said spectrometer in a case where a standard object having a known reflectance characteristic is disposed at said first window instead of said object to be measured.

2. The quantum efficiency measurement apparatus according to claim 1, wherein
   said first window is configured such that said object to be measured can be attached in a state where an exposed surface of said object to be measured substantially coincides with a surface of said plane mirror, said surface of said plane mirror being located on an inner side of said hemispheric portion.

3. The quantum efficiency measurement apparatus according to claim 1, wherein
said second window includes a light transmission diffusion member disposed between an inside of said hemispheric portion and said spectrometer.

4. A quantum efficiency measurement apparatus comprising:
a hemispheric portion with an inner surface having a light diffuse reflection layer;
a plane mirror disposed to pass through a substantial center of curvature of said hemispheric portion and close an opening of said hemispheric portion, said plane mirror including a first window provided near the substantial center of curvature of said hemispheric portion and a second window provided at a position apart by a predetermined distance from said first window;
a light source for applying an excitation light through said first window toward an object to be measured disposed in a state where at least a part of the object to be measured is exposed in said hemispheric portion;
a spectrometer for measuring a spectrum in said hemispheric portion through said second window, said second window restraining light from said object to be measured from directly entering said spectrometer; and
a processor for calculating a quantum efficiency of said object to be measured, based on a first spectrum measured by said spectrometer in a case where said object to be measured is disposed in said hemispheric portion, and a second spectrum measured by said spectrometer in a case where a standard object having one of a known reflectance characteristic and a known transmittance characteristic is disposed in said hemispheric portion instead of said object to be measured.

5. The quantum efficiency measurement apparatus according to claim 4, wherein
said second window is an opening having a larger diameter on an outer side of said hemispheric portion than a diameter of said opening on an inner side of said hemispheric portion.

6. The quantum efficiency measurement apparatus according to claim 4, wherein
said hemispheric portion includes a third window provided at a position where said hemispheric portion intersects with a normal that is normal to said plane minor and passes through the substantial center of curvature of said hemispheric portion, for attaching said object to be measured and said standard object to said third window, and
said light source is disposed to apply said excitation light at a predetermined angle with respect to the normal to said plane mirror toward said third window.

7. The quantum efficiency measurement apparatus according to claim 4, wherein
said object to be measured is a liquid enclosed in a transparent container and is disposed on an optical axis of said light source.

8. The quantum efficiency measurement apparatus according to claim 7, wherein
said object to be measured is entirely contained in said hemispheric portion.

9. The quantum efficiency measurement apparatus according to claim 4, wherein
said hemispheric portion includes a third window provided at a position where said hemispheric portion intersects with a normal that is normal to said plane minor and passes through the substantial center of curvature of said hemispheric portion, for attaching said object to be measured and said standard object to said third window,
said first window is provided at a position of the substantial center of curvature of said hemispheric portion on said plane mirror, and
said object to be measured is a liquid enclosed in a tubular container, a surface of said tubular container that is attached to said third window is formed of a transparent material, and a remaining part of said tubular container is formed of a light-reflective member.

10. A quantum efficiency measurement method comprising the steps of:
preparing an apparatus including a hemispheric portion with an inner surface having a light diffuse reflection layer, and a plane minor disposed to pass through a substantial center of curvature of said hemispheric portion and close an opening of said hemispheric portion;
attaching an object to be measured to a first window provided at a position of said plane mirror, said position including the substantial center of curvature of said hemispheric portion;
applying an excitation light, through a third window provided in said hemispheric portion, at a predetermined angle with respect to a normal to said plane minor toward said object to be measured;
measuring, as a first spectrum, a spectrum in said hemispheric portion in a case where said object to be measured is attached, through a second window provided at a position of said plane mirror, said position being apart by a predetermined distance from said first window;
attaching a standard object having a known reflectance characteristic to said first window;
applying said excitation light through said third window, at said predetermined angle with respect to the normal to said plane minor toward said standard object;
measuring, as a second spectrum, a spectrum in said hemispheric portion through said second window in a case where said standard object is attached; and
calculating a quantum efficiency of said object to be measured, based on said first spectrum and said second spectrum.

* * * * *